United States Patent [19]

Hester

[11] Patent Number: 5,312,550

[45] Date of Patent: May 17, 1994

[54] METHOD FOR DETECTING UNDESIRED DIALYSIS RECIRCULATION

[76] Inventor: Robert L. Hester, 1426 Tracewood Dr., Jackson, Miss. 39211

[21] Appl. No.: 873,781

[22] Filed: Apr. 27, 1992

[51] Int. Cl.$^5$ .............................................. B01D 61/32
[52] U.S. Cl. ................................. 210/646; 210/96.2; 210/745; 210/805; 436/164; 604/4
[58] Field of Search ............... 210/94, 96.1, 321.71, 210/646, 647, 745, 96.2, 805; 422/82.09; 436/56, 164; 604/4, 5, 6

[56] References Cited

U.S. PATENT DOCUMENTS

| 3,482,575 | 12/1969 | Claff et al. | 604/4 |
| 3,619,423 | 11/1971 | Galletti et al. | 210/646 |
| 4,181,610 | 1/1980 | Shintani et al. | 210/96.2 |
| 5,092,836 | 3/1992 | Polaschegg | 210/646 |

FOREIGN PATENT DOCUMENTS

| 521891 | 7/1976 | U.S.S.R. | 604/5 |
| 1013853 | 4/1983 | U.S.S.R. | 604/4 |

*Primary Examiner*—Joseph W. Drodge
*Attorney, Agent, or Firm*—Kelly D. Corley

[57] ABSTRACT

In a dialysis system wherein blood is removed from a patient's vascular system and passed through a dialyzer system comprising an inlet arterial line, a dialyzer, and an outlet venous line, the blood being fed via the inlet arterial line to the dialyzer and returned to the patient via the outlet venous line, a material having a physical property differing from that of blood is injected at a point in the venous return line. The fluid in the dialysis system upstream from the injection point is monitored for the presence of the different physical property whereby direct recirculation from the venous return line to the arterial intake line is detected.

5 Claims, 1 Drawing Sheet

METHOD FOR DETECTING UNDESIRED DIALYSIS RECIRCULATION

The invention relates to the field of kidney dialysis processes, and more particularly to such processes for detecting undesirable recirculation of the dialyzed blood.

Dialysis is a process by which an artificial kidney replaces the function of a patient's kidney. Blood is removed from the patient's vascular system via an arterial line, passed through a dialyzer, and returned to the patient via a venous line for normal circulation through the patient's vascular system. A majority of patients have an arterial-venular shunt implanted to accommodate the high rate of blood flow, which typically is about 350 ml/minute. However, if there is a problem with the venous outflow, freshly dialyzed blood returning to the patient via the venous line can pass upstream through the shunt and return directly to the arterial line where it is again filtered. If this undesired direct recirculation level is high enough, a small amount of blood is repeatedly refiltered and the rest of the patient's blood is not sufficiently filtered to provide the patient with adequate dialysis.

The standard test for undesired direct recirculation requires three blood samples while the patient is on dialysis. This method of determining recirculation requires blood samples from the patient, technical time from the nurses, and high laboratory costs. Dialysis patients have lower hematocrit than the normal population, and thus cannot afford to lose blood.

These and other problems with prior art practice are avoided by the present invention, which provides an accurate determination of undesired recirculation at lower cost.

According to a principal aspect of the invention, there is provided in a dialysis process wherein blood is removed from a patient's vascular system and passed through a dialyzer system comprising an inlet arterial line, a dialyzer, and an outlet venous line, the blood being fed via the inlet arterial line to the dialyzer and returned to the patient via the outlet venous line, the improvement comprising injecting a material at an injection point in the dialyzer system, the material having a physical property differing from that of blood, and monitoring the fluid in the dialyzer system at a point upstream from the injection point for the presence of the differing physical property, to thereby detect undesired recirculation of freshly dialyzed blood from the venous line directly to the arterial line.

According to another aspect of the invention, the material is a saline solution substantially isotonic with blood.

According to another aspect of the invention, the step of monitoring comprises measuring the optical density of the fluid.

Other aspects will in part appear hereinafter and will in part be apparent from the following detailed description taken together with the accompanying drawings, wherein.

Figure 1:
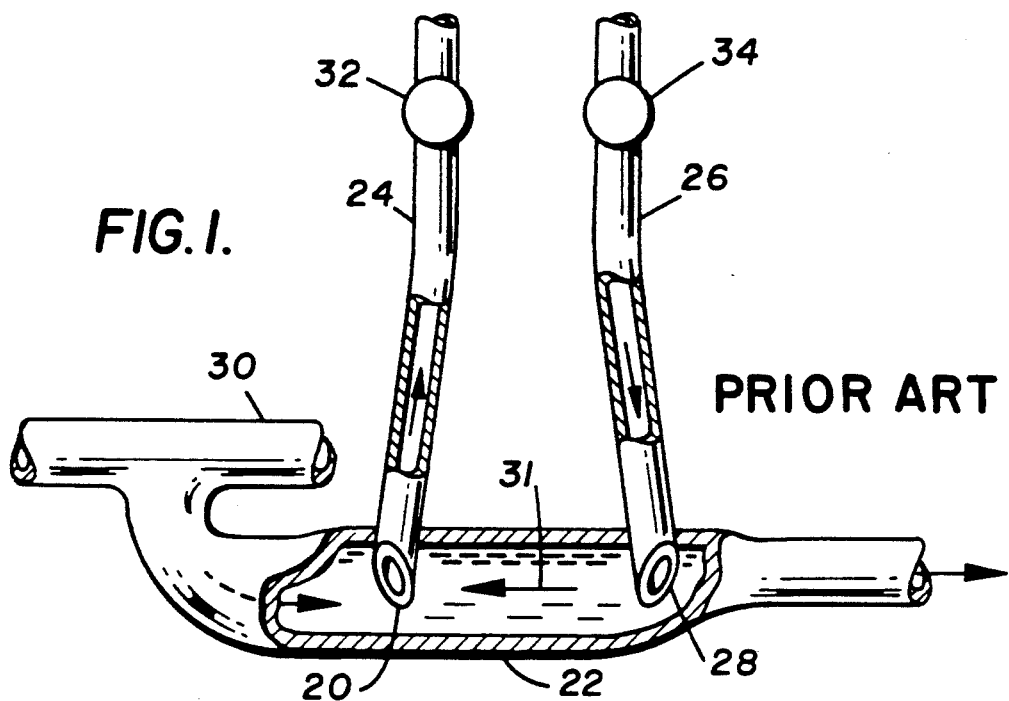
FIG. 1 is a schematic elevation view of the prior art.

Referring to FIG. 1, blood is removed from upstream location 20 in blood vessel 22 and passed through arterial line 24 to a non-illustrated dialyzer, then returned from the dialyzer via venous line 26, to downstream location 28 in vessel 22. Vessel 22 is illustrated as an arterial-venular shunt connected at its upstream end to artery 30 and connected at its downstream end to a non-illustrated downstream blood vein. If the downstream vein presents an unduly high resistance to the outflow of dialyzed blood issuing from venous line 26, part of the freshly dialyzed blood will flow back to upstream location 20 as indicated by arrow 31, and will be returned via line 24 to the dialyzer.

To prevent such undesired recirculation, current practice is to remove a blood sample from artery 30, another from sampling port 32, and a third from sampling port 34. These samples are then chemically analyzed to determine the amounts of certain constituent chemicals contained therein, from which the degree of undesired recirculation, if any, may be calculated. These chemical analyses are costly and time consuming. On occasion, dialysis is completed before the analyses determine that excessive undesired recirculation has occurred. In such an instance, some hours of dialysis have done the patient little good.

Figure 2:
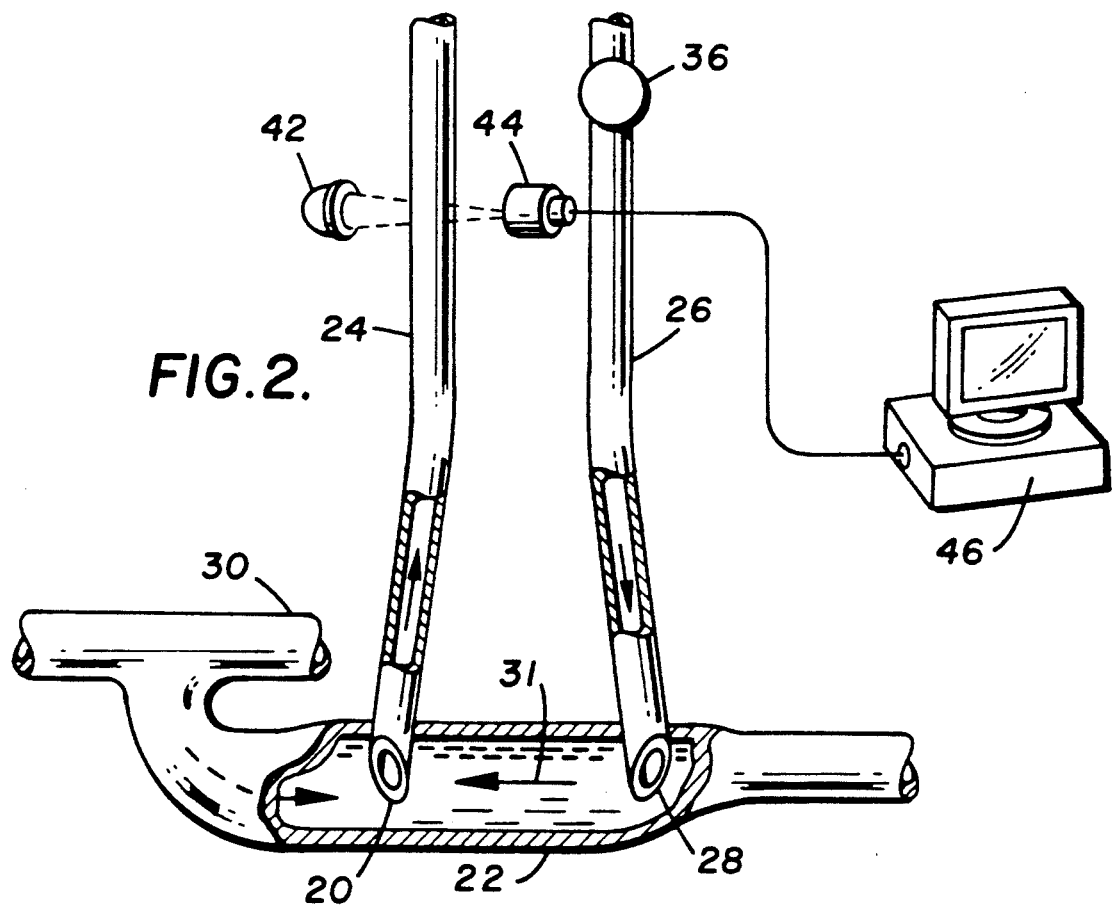
FIG. 2 is a similar schematic elevation view of the preferred embodiment of the present invention.

The preferred embodiment of the present invention is illustrated in FIG. 2. As illustrated therein, a material having a selected physical property differing from that of blood is injected into venous line 26 through injection port 36. In the preferred embodiment, this material is a saline solution isotonic with blood. Such a saline solution differs from blood in color, and the amount of saline solution intermixed with blood can readily be determined optically. Accordingly, a detector is provided at a location upstream of injection port 36, preferably as illustrated in line 24. The detection comprises light source 42 shining light through the fluid passing through line 24, and photodetector 44 produces an output signal related to the optical density of the fluid. The output signal is fed to computer 46 where it is analyzed.

Injection of 10 ml. of saline dilutes the freshly dialyzed blood flowing through venous line 26, making it more transparent. If there is direct recirculation from location 28 to location 20, some of the saline solution will be carried into arterial line 24, resulting in an increase in light intensity detected by photodetector 44 and a resulting change in the output signal produced thereby.

With this method of determining the presence and amount of recirculation, no blood is taken from the patient, the results are known in minutes rather than hours, and costs are substantially reduced.

While the above example uses an isotonic saline solution, other materials and other physical properties than optical properties may be used.

I claim:

1. In a dialysis process wherein blood is removed from a patient's vascular system and passed through a dialyzer system comprising an inlet arterial line, a dialyzer, and an outlet venous line, said blood being fed via said inlet arterial line to said dialyzer and returned to the patient via said outlet venous line, the improvement comprising:
   (a) injecting a material at an injection point in said dialyzer system, said material having a physical property differing from that of blood; and
   (b) monitoring the fluid in said dialyzer system at a point in said dialyzer system upstream from said injection point for the presence of said differing physical property, to thereby detect undesired recirculation of freshly dialyzed blood from said venous line directly to said arterial line.

2. The process defined in claim 1, wherein said material is a saline solution substantially isotonic with blood.

3. The process defined in claim 2, wherein said step of monitoring comprises measuring the optical density of said fluid.

4. The process defined in claim 1, wherein said step of monitoring comprises measuring the optical density of said fluid.

5. The proces defined in claim 1, wherein said injection point is in said venous line.

* * * * *

REEXAMINATION CERTIFICATE (3142nd)

United States Patent [19]
Hester

[11] B1 5,312,550
[45] Certificate Issued Feb. 25, 1997

[54] METHOD FOR DETECTING UNDESIRED DIALYSIS RECIRCULATION

[76] Inventor: Robert L. Hester, 1426 Tracewood Dr., Jackson, Miss. 39211

Reexamination Request:
No. 90/003,794, Apr. 14, 1995

Reexamination Certificate for:
Patent No.: 5,312,550
Issued: May 17, 1994
Appl. No.: 873,781
Filed: Apr. 27, 1992

[51] Int. Cl.⁶ .................................................. B01D 61/32
[52] U.S. Cl. .................... 210/646; 210/96.2; 210/745; 210/805; 436/164; 604/4
[58] Field of Search .......................... 210/94, 96.1, 96.2, 210/321.71, 646, 647, 745, 805, 739; 422/82.09; 436/56, 164; 604/4, 5, 6; 128/632, 633

[56] References Cited

U.S. PATENT DOCUMENTS

| | | | |
|---|---|---|---|
| 3,482,575 | 12/1969 | Claff et al. | 604/4 |
| 3,619,423 | 11/1971 | Galletti et al. | 210/646 |
| 5,092,836 | 3/1992 | Polaschegg | 210/646 |

FOREIGN PATENT DOCUMENTS

| | | | |
|---|---|---|---|
| 521891 | 7/1976 | U.S.S.R. | 604/5 |
| 1013853 | 4/1983 | U.S.S.R. | 604/4 |

OTHER PUBLICATIONS

Aldridge et al, "The assessment of arteriovenous fistulae created from pressure and thermal dilution measurements," Journal of Medical Engineering and Technology, vol. 8, No. 3, May/Jun. 1984, pp. 118–124.

Greenwood et al, "Assessment of arteriovenous fistulae from pressure and thermal dilution studies; clinical experience in forearm fistulae," Clinical Nephrology, vol. 23, No. 4 (1985), pp. 189–197.

*Primary Examiner*—Joseph Drodge

[57] ABSTRACT

In a dialysis system wherein blood is removed from a patient's vascular system and passed through a dialyzer system comprising an inlet arterial line, a dialyzer, and an outlet venous line, the blood being fed via the inlet arterial line to the dialyzer and returned to the patient via the outlet venous line, a material having a physical property differing from that of blood is injected at a point in the venous return line. The fluid in the dialysis system upstream from the injection point is monitored for the presence of the different physical property whereby direct recirculation from the venous return line to the arterial intake line is detected.

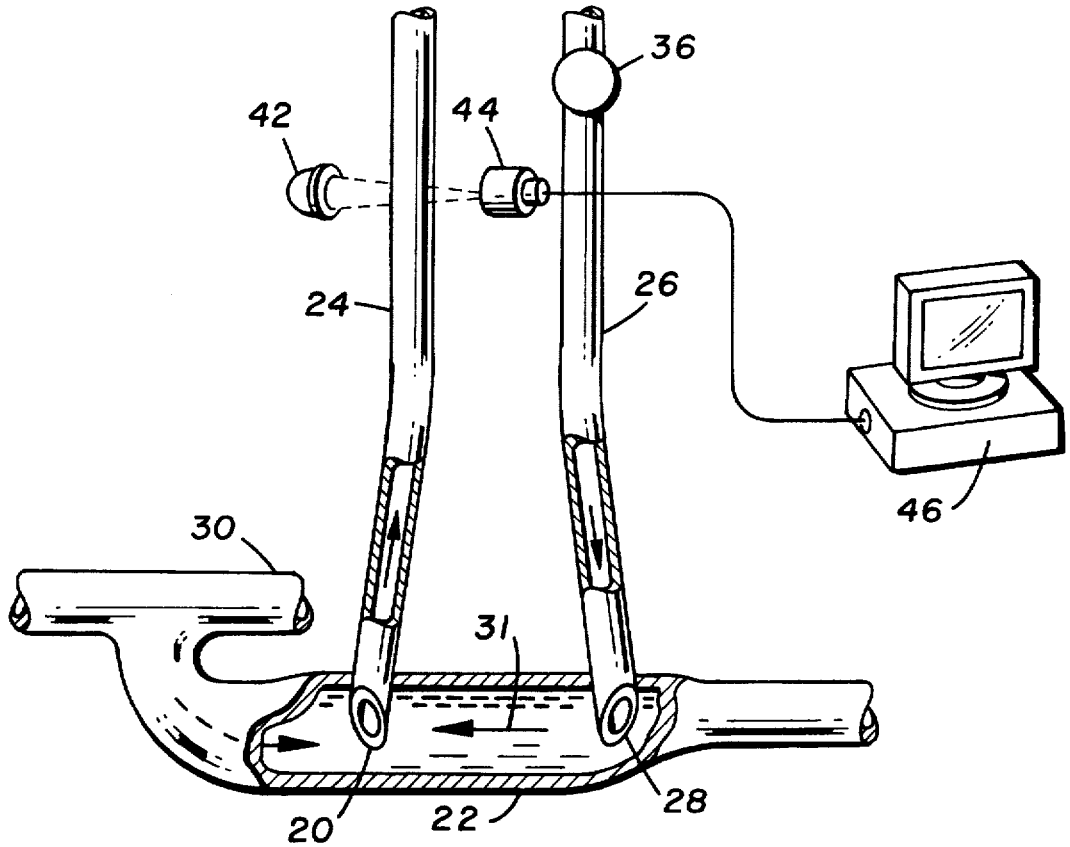

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–5 is confirmed.

New claim 6 is added and determined to be patentable.

*6. The process of claim 4 wherein the monitoring of optical density is by a detector comprising a light source shining light through fluid passing through the arterial line and a photo detector detecting the light and producing an output signal related to the optical density of the fluid.*

* * * * *